United States Patent [19]

Carenzi et al.

[11] Patent Number: 4,764,530

[45] Date of Patent: Aug. 16, 1988

[54] PHARMACEUTICAL COMPOSITIONS AND THEIR USE AS MYDRIATICS

[76] Inventors: Angelo Carenzi, Via Rossini, 9, 21051 Busto Arsizio; Oreste Cerri, Viale Campania, 21, 20133 Milano; Franco Pozzi, Via Jacopo Rezia, 11, 22100 Como; Cesare Casagrande, Via Campo Gallo, 21/67, 20020 Arese; Giovanna Miragoli, Corso Italia, 1, 20122 Milano; Michele Virno, Via Papiniano, 29, 00137 Rome, all of Italy

[21] Appl. No.: 909,119

[22] PCT Filed: Dec. 24, 1985

[86] PCT No.: PCT/EP85/00744

§ 371 Date: Aug. 20, 1986

§ 102(e) Date: Aug. 20, 1986

[87] PCT Pub. No.: WO86/03970

PCT Pub. Date: Jul. 17, 1986

[30] Foreign Application Priority Data

Dec. 27, 1984 [IT] Italy .................................. 24266 A/84

[51] Int. Cl.$^4$ ............................................. A61K 31/225
[52] U.S. Cl. ...................................... 514/548; 514/912
[58] Field of Search .................................. 514/548, 912

[56] References Cited

U.S. PATENT DOCUMENTS

| | | | |
|---|---|---|---|
| 3,959,485 | 5/1976 | Windheuser | 514/548 |
| 4,218,470 | 8/1980 | Casagrande et al. | 514/548 |
| 4,275,074 | 6/1981 | Langham et al. | 514/646 |
| 4,628,064 | 12/1986 | Casagrande et al. | 514/654 |

FOREIGN PATENT DOCUMENTS

| | | | |
|---|---|---|---|
| 0067910 | 12/1982 | European Pat. Off. | 59/39 |
| 0105840 | 4/1984 | European Pat. Off. | 366/42 |
| 2360558 | 3/1978 | France | 33/178 B |

OTHER PUBLICATIONS

Ocular Pharmacology—4th Ed.—1978, The C.V. Mosby Co.—St. Louis, MO.—p. 237.

Primary Examiner—Douglas W. Robinson
Attorney, Agent, or Firm—Cushman, Darby & Cushman

[57] ABSTRACT

Pharmaceutical compositions and their use in ophthalmology. Said compositions comprise ibopamine (epinine 3, 4-0-diisobutyrate and are used mainly as mydriatics.

2 Claims, No Drawings

PHARMACEUTICAL COMPOSITIONS AND THEIR USE AS MYDRIATICS

This invention relates to new pharmaceutical compositions and their use in ophthalmology.

More particularly this invention relates to new pharmaceutical compositions comprising ibopamine or a pharmaceutically acceptable addition salt thereof, and to their use as mydriatics.

Ibopamine (epinine 3,4-O-diisobutyrate) is a drug useful for systemic use in cardiovascular therapy (U.S. Pat. No. 4,218,470).

Now it has been found that ibopamine administered locally shows a considerable mydriatic effect and thus has different ophthalmological applications both in diagnosis, for examination of the fundus and refraction, and in ophthalmic surgery when it is desired to antagonize intraoperative myosis.

Although the use of sympathomimetic amines as mydriatics is conceptually a potentially beneficial alternative to the use of anticholinergic agents the only sympathomimetic agent finding limited use as a mydriatic is phenylephrine.

Phenylephrine has a moderate action and is not free of drawbacks because of systemic effects shown at the high concentrations (from 10 to 36%) which must be used to obtain the desired effect. Also the other available sympathomimetic drugs, particularly adrenaline are not free from drawbacks concerning local tolerability and the risk of systemic effects.

Suprisingly ibopamine has proven to be well suited as a mydriatic agent.

Ibopamine exhibits a strong mydriatic effect which is associated to an excellent pharmacodynamic profile characterized by rapid onset and subsequent rapid exhaustion of the effect with considerable benefit for the patient.

Along with this favourable profile of effectiveness it shows a very good local tolerability and absence of systemic side effects.

With respect to the atropine-like compounds which are the drugs most commonly used as mydriatics ibopamine has the advantage of producing a rapid onset of the effect which lasts just for a period of time consistent with the needs of the ophthalmological examination and is more rapidly exhausted. This behaviour is very favourable in ophthalmic diagnosis allowing rapid recovery of normal visual functions of the patient.

The mydriatic effect of the compounds was evaluated on male New Zealand rabbits weighing 2.5-3 kg in accordance with the following method.

The animals were placed in retention cages in a room lit with artificial light.

The diameter of the pupil was measured with a gauge (to 1/10 mm) and with the aid of a magnifying glass (1.5 diameters).

The compounds were dissolved in physiological solution and instilled in a 0.1 ml volume in the conjunctival sac of one eye while the contra-lateral eye was treated with an equal volume of physiological solution.

In the control animals physiological solution was instilled in both eyes.

The mydriatic effect of ibopamine was tested in comparison with adrenaline, adrenaline diisobutyrate and dipivalate, epinine and epinine dipivalate (U.S. Pat. No. 4,218,470 mentioned above) (Table 1).

Local tolerability and systemic effects in the rabbit, more particularly pressor effects (Table 1) were also investigated.

TABLE 1

Effect on the rabbit after conjuctival instillation.

| Substance | Concentration [mM][1] | Tolerability (conjunctival irritation and relative concentration [mM][2]) | Blood pressure variation[3] (mmHg) |
|---|---|---|---|
| Epinine HCl | 100 | −(100) | −7 |
| Epinine 3,4-O—diisobutyrate hydrochloride | 6.2 | −(100) | −7 |
| Epinine 3,4-O—dipivalate hydrochloride | 6.2 | +(50) | not tested |
| dl-Adrenaline HCl | 6.2 | −(50) | +48 |
| dl-Adrenaline 3,4-O—diisobutyrate HCl | 12.5 | −(50) | +40 |
| dl-Adrenaline 3,4-O—dipivalate hydrochloride | 3.1 | +(50) | +35 |

[1]Concentrations causing an increase in pupil diameter of comparable degree (approximately 1 mm).
[2]+ present; − absent.
[3]Instillation of 0.1 ml of 0.5 M solution.

The results shown in Table 1 prove that ibopamine is endowed with high mydriatic effect, with good local tolerability and absence of side effects.

Epinine proved to exhibit slight mydriatic effect while adrenaline proved to be effective experimentally but it is well-known that its clinical use is riskful because of systemic effects, which are evident also from the blood pressure increase which occured in the experimental animal.

Epinine dipivalate proved to be as effective as ibopamine but was irritating at nearly mydriatic concentrations.

Similarly, adrenaline dipivalate showed poor separation between the active dose and the dose which induce irritation and systemic effects while adrenaline diisobutyrate proved less active than adrenaline as a mydriatic agent although it showed significant systemic effects.

As a matter of fact, adrenaline dipivalate (dipivefrine) is used clinically only in low doses in the therapy of glaucoma.

Ibopamine therefore possesses to a surprising degree characteristics of effectiveness, absence of undesired systemic effects, and excellent local tolerability, characteristics not possessed simultaneously by epinine and by other catecholamines or their derivatives.

Additional experiments to confirm the safety of ibopamine compared with (±)-adrenaline, (±)-adrenaline dipivalate and phenylphrine were performed by intravenous administration in the anesthetized rabbit. The three reference drugs induced hypertension in the following order of strength: (±) -adrenaline>phenylephrine>(±)adrenaline dipivalate. Ibopamine did not induce hypertension but a moderate reduction of blood pressure. The results are given in Table 2.

TABLE 2

Effect on blood pressure and on heart rate in rabbit.

| Compound | Dose/kg iv μg | μmol | Number of animals | Variation in mean blood pressure m ± E.S. |
|---|---|---|---|---|
| Ibopamine HCl | 3.4 | 0.01 | 3 | −10 ± 7.5 |
|  | 6.8 | 0.02 | 3 | −14 ± 6.4 |
|  | 13.6 | 0.04 | 3 | −13 ± 6.4 |
|  | 27.2 | 0.0 | 3 | −18 ± 2.2 |
|  | 54.4 | 0.16 | 3 | −12 ± 4.1 |

TABLE 2-continued

Effect on blood pressure and on heart rate in rabbit.

| Compound | Dose/kg iv μg | Dose/kg iv μmol | Number of animals | Variation in mean blood pressure m ± E.S. |
|---|---|---|---|---|
| | 108.8 | 0.32 | 2 | −17 ± 7.8 |
| dl-Adrenaline HCl | 1.8 | 0.01 | 5 | 22 ± 3.8 |
| | 3.6 | 0.02 | 5 | 32 ± 4.6 |
| | 7.2 | 0.04 | 3 | 49 ± 3.5 |
| | 14.4 | 0.08 | 3 | 65 ± 9.3 |
| | 28.8 | 0.16 | 2 | 100 ± 4.5 |
| dl-Adrenaline 3,4-O— dipivalate HCl | 3.8 | 0.01 | 2 | 0 |
| | 7.6 | 0.02 | 3 | 1 ± 4.8 |
| | 15.2 | 0.04 | 3 | 7 ± 7.2 |
| | 30.4 | 0.08 | 3 | 6 ± 2.4 |
| | 60.8 | 0.16 | 2 | 30 ± 4.5 |
| Phenylephrine HCl | 2.3 | 0.01 | 1 | 5 |
| | 4.6 | 0.02 | 2 | 14 ± 3.5 |
| | 9.2 | 0.04 | 3 | 18 ± 3.0 |
| | 18.4 | 0.08 | 3 | 23 ± 2.7 |
| | 36.8 | 0.16 | 3 | 30 ± 3.1 |
| | 73.6 | 0.32 | 3 | 48 ± 4.2 |

In the case of ibopamine, the absence of side effects was confirmed by clinical tests in humans in which maximal mydriasis was observed by instilling 1–2 drops of 2% collyrium. Mydriasis begins in 15–30 minutes and recedes after approximately 1 hour. Blood pressure and heart rate are unchanged.

In case of phenylephrine increases in blood pressure were observed in particular in children (Barromeo Mac-Grail et al, Ocular Therapeutics, 1980, 119).

Ibopamine and the pharmaceutically acceptable acid addition salts thereof, preferably hydrochloride, may be formulated in suitable pharmaceutical preparations.

Suitable pharmaceutical forms are those normally used in ophthalmology such as collyria and ointments.

Said preparation comprise an effective amount of ibopamine or a salt thereof together with pharmaceutically acceptable diluents, preservatives, buffers, stabilizing agent and the like.

The amount of ibopamine or of a salt thereof may range from 0.01 to 10% (w/v) and preferably from 0.1 to 5%.

The collyrium may be preformed or instantly prepared by dilution of a suitable solid or liquid pharmaceutical form.

In preparing these pharmaceutical forms the skilled in the art will pay due attention to those conditions of concentration, pH and ionic strength which ensure at the same time adequate stability and optimal tolerability and allow transcorneal absorption of the drug.

It has been found that these optimal requirements are met for example by a formulation of ibopamine hydrochloride in crystallized or lyophilized sterile powder, optionally in combination with suitable excipients such as mannitol and polyvinylpyrrolidone; the preparation is dissolved before use in water or in a sterile saline solution, for example of sodium chloride, or in a sterile buffer solution suitable to obtain a pH between 4 and 6. The amount of ibopamine hydrochloride and the concentration of the saline and buffer solutions are balanced in such a manner as to obtain solutions having ionic concentrations suitable for the purposes of stability and absorption; ibopamine hydrochloride concentration ranges between 0.5 and 5%. The solutions may contain a suitable preservative such as benzalkonium chloride, an antioxidant such as ascorbic acid or sodium metabisulphate or a sequestrating agent such as ethylendiaminetetracetic acid and its salts.

To better illustrate this invention the following examples are given.

EXAMPLE 1

A solution having the following composition (for 1 ml) is formed at the time of use:

| (a) | Crystallized ibopamine HCl sterile powder | 20.00 mg |
|---|---|---|
| (b) | Sterile solution of:- | |
| | citric acid monohydrate | 5.72 mg |
| | disodium phosphate.12H$_2$O | 16.27 mg |
| | benzalkonium chloride | 0.10 mg |
| | sodium chloride | 1.00 mg |
| | in distilled water (q.s. to 1 ml) | |

The ingredients are filled into a suitable container of from 1 to 10 ml capacity fitted with a dropper.

EXAMPLE 2

A solution having the following composition (for 1 ml) is formed at time of use:

| (a) | Sterile lyophilized mixture of:- | |
|---|---|---|
| | ibopamine HCl | 10.0 mg |
| | mannitol | 20.0 mg |
| (b) | Sterile solution of: benzalkonium chloride | 0.1 mg |
| | in distilled water (q.s. to 1 ml) | |

The ingredients are filled into a suitable container of from 1 to 10 ml capacity fitted with a dropper.

We claim:

1. A method for inducing a mydriatic effect in a subject in need of such effect, said method comprising administering to one or both eyes of said subject a mydriatically effective amount of an ophthalmic collyrium containing from 0.01 to 10% (w/v) of ibopamine or a pharmaceutically acceptable acid addition salt thereof.

2. The method of claim 1, wherein the amount of ibopamine or pharmaceutically acceptable acid addition salt thereof is in the range of 0.1 to 5% (w/v).

* * * * *